United States Patent [19]

Häussling et al.

[11] Patent Number: 5,750,788
[45] Date of Patent: May 12, 1998

[54] PREPARATION OF AMINES FROM COMPOUNDS HAVING AT LEAST 3 CYANO GROUPS

[75] Inventors: Lukas Häussling, Bad Dürkheim; Horst Neuhauser, Dudenhofen; Wolfgang Paulus, Weisenheim, all of Germany

[73] Assignee: BASF Aktiengesellschaft, Ludwigshafen, Germany

[21] Appl. No.: 849,102

[22] PCT Filed: Nov. 9, 1995

[86] PCT No.: PCT/EP95/04408

§ 371 Date: May 12, 1997

§ 102(e) Date: May 12, 1997

[87] PCT Pub. No.: WO96/15097

PCT Pub. Date: May 23, 1996

[30] Foreign Application Priority Data

Nov. 12, 1994 [DE] Germany .......... 44 40 551.0

[51] Int. Cl.⁶ .................................................. C07C 209/48
[52] U.S. Cl. .................. 564/415; 502/324; 564/448; 564/491; 564/492
[58] Field of Search .................. 564/415, 448, 564/491, 492; 502/324

[56] References Cited

U.S. PATENT DOCUMENTS 3,565,957  2/1971  Mirviss et al. ............... 260/583
5,105,015  4/1992  Lin et al. ..................... 564/490

*Primary Examiner*—Brian M. Burn
*Attorney, Agent, or Firm*—John H. Shurtleff

[57] ABSTRACT

A process is disclosed for preparing amines by hydrogenating compounds with at least 3 cyano groups prepared by adding acrylonitrile to ammonia or primary amines at temperatures from 80° to 200° C. and pressures from 5 to 500 bars. Hydrogenation is carried out continuously on a catalyst that contains 80 to 98% by weight cobalt oxide, 1 to 10% by weight manganese oxide, 1 to 10% by weight phosphorus pentoxide and 0 to 5% by weight alkali metal oxides

10 Claims, No Drawings

PREPARATION OF AMINES FROM COMPOUNDS HAVING AT LEAST 3 CYANO GROUPS

The present invention relates to a continuous process for preparing amines by hydrogenation of compounds having at least 3 cyano groups, prepared by addition of acrylonitrile onto ammonia or primary amines, at elevated temperatures and elevated pressure on novel cobalt catalysts.

Angew. Chem. 105 (1993) 1367 to 1372 discloses the batchwise reduction of nitrites with hydrogen on Raney cobalt in methanolic solution.

DE-A-27 39 917 discloses catalysts for the hydrogenation of cyanoethylated amines which contain cobalt or nickel as catalysts on a suitable support.

The batchwise process disclosed to date for reducing multiply cyano-containing compounds are not economically attractive for production on the industrial scale.

Accordingly, a novel and improved process for preparing amines by hydrogenation of compounds having at least 3 cyano groups, prepared by addition of acrylonitrile onto ammonia or primary amines, at from 80° to 200° C. under from 5 to 500 bar has been found and comprises carrying out the hydrogenation continuously on a catalyst which contains from 80 to 98% by weight of cobalt oxides, from 1 to 10% by weight of manganese oxide, from 1 to 10% by weight of phosphorus pentoxide and from 0 to 5% by weight of alkali metal oxides, and novel cobalt catalysts.

The hydrogenation according to the invention can be carried out in the following way:

The amino nitrile which has formed on acrylonitrile addition onto ammonia or primary amines and has one or more cyano groups can be reacted in the presence or absence of ammonia in the presence of hydrogen at from 80° to 200° C., preferably 100° to 160° C., particularly preferably 110° to 150° C., under from 5 to 500 bar, preferably 50 to 300 bar, particularly preferably 100 to 250 bar, on a catalyst which contains from 80 to 98% by weight of cobalt oxide, from 1 to 10% by weight of manganese oxide and from 1 to 10% by weight of phosphorus pentoxide and from 0 to 5% by weight of alkali metal oxide, preferably from 86 to 94% by weight of cobalt oxide, from 3 to 7% by weight of manganese oxide and from 3 to 7% by weight of phosphorus pentoxide and from 0 to 5% by weight of alkali metal oxide, particularly preferably from 88 to 92% by weight of cobalt oxide, from 4 to 6% by weight of manganese oxide, from 4 to 6% by weight of phosphorus pentoxide and from 0 to 4% by weight of alkali metal oxide, as a rule in an inert solvent.

The abovementioned cobalt catalysts, excepting Raney cobalt, can be used as catalysts on inert supports such as alumina, silica, titanium oxide, zirconium oxide or zeolites of the pentasil, faujasite, X or Y type or, preferably, as unsupported catalysts. These cobalt catalysts preferably consist only of cobalt oxide, manganese oxide, phosphorus pentoxide and alkali metal oxide, preferably $Na_2O$, where appropriate on inert supports. The preparation of the catalysts to be used according to the invention is described, for example, in DE-A 43 25 847 and in German Patent Applications 19516845 and 19507398.

The hydrogenation can also be carried out without ammonia. However, ammonia as a rule is preferably used in gas or liquid form, but generally not in aqueous solution, in a ratio of mol of ammonia per cyano group of the amino nitrile formed as inetrmediate of from 1:1 to 10,000:1, preferably from 1.5:1 to 3000:1, particularly preferably from 2:1 to 1000:1. The excess of ammonia can also be more than 10,000:1 without problems.

The hydrogen is generally introduced into the reaction in an amount of from 5 to 400 l(STP), preferably in an amount of from 50 to 200 l(STP) per mol of amino nitrile.

The practical procedure for the reaction is to feed the amino nitrile in an inert solvent and ammonia simultaneously to the heterogeneous catalyst, which is normally located in a fixed bed reactor which is preferably heated from outside, at the required temperature under the required pressure. The space velocity is generally from 0.001 to 5.0, preferably 0.005 to 2.0 and, particularly preferably, from 0.01 to 1.5 l of amino nitrite per liter of cobalt catalyst and hour.

It is possible for the reactants to be passed either from bottom to top or from top to bottom through the reactor.

The reaction is carried out continuously. It is possible for the excess ammonia to be circulated together with the hydrogen. If the conversion in the reaction is incomplete, the unreacted starting material can likewise be returned to the reaction zone.

The excess ammonia and the hydrogen can be removed from the discharge from the reaction, after the pressure has expediently been reduced, and if desired the resulting product can be purified, for example by distillation or extraction. Ammonia and hydrogen can advantageously be returned to the reaction zone. The same applies to any amino nit-rile which has not completely reacted.

The water formed during the reaction generally has no adverse effect on the degree of conversion, the reaction rate, the selectivity and the life of the catalyst and can therefore expediently be removed from the reaction product only when it is distilled.

Suitable inert solvents are alcohols, e.g. $C_1$–$C_{20}$-alkanols, preferably $C_1$–$C_8$-alkanols, particularly preferably $C_1$–$C_4$-alkanols, such as methanol and ethanol, ethers, e.g. aliphatic $C_4$–$C_{20}$-ethers, preferably $C_4$–$C_{12}$-ethers, such as diethyl ether, methyl isopropyl ether and methyl tert-butyl ether, cyclic ethers such as tetrahydrofuran and dioxane, glycol ethers such as ethylene glycol dimethyl ether, dimethylformamide and saturated nitrogen heterocycles with tertiary nitrogen such as N-methylpyrrolidone.

Suitable primary amines for the acrylonitrile addition and the subsequent hydrogenation according to the invention are those of the general formula I $$(R^1R^1)N-X-N(R^1R^1)$$ (I), where $R^1$ is hydrogen or 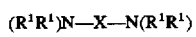 $(R^2R^2)N-(CH_2)_3-$ and $R^2$ is hydrogen or $(R^3R^3)N-(CH_2)_3-$ and $R^3$ is hydrogen or $(R^4R^4)N-(CH_2)_3-$ and $R^4$ is hydrogen or $(R^5R^5)N-(CH_2)_3-$ and $R^5$ is hydrogen or $(R^6, R^6)N-(CH_2)_3-$ and $R^6$ is hydrogen, and X is

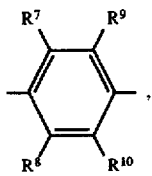

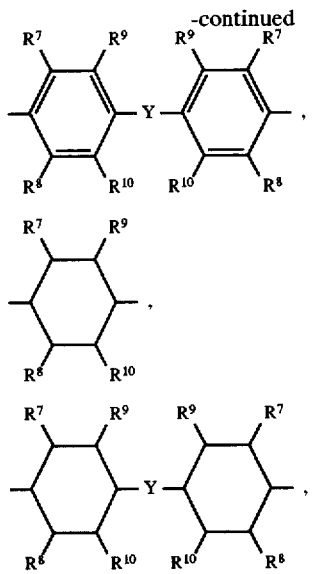

—(CH$_2$)$_n$—, —(CH$_2$)$_3$—NR$^{11}$—(CH$_2$)$_3$—,C$_2$-C$_{20}$-alkylene, —(CH$_2$)$_l$—[O—(CH$_2$)$_k$]$_m$—O—(CH$_2$)$_l$)— and Y is CR$^7$R$^9$, oxygen, C=O, SO$_2$, n is 2–20, 1 and k are 2–6, and m is 1–40, R$^7$, R$^8$, R$^9$, R$^{10}$ are hydrogen or C$_1$–C$_6$-alkyl, R$^{11}$ is C$_1$-C$_{20}$-alkyl, C$_2$-C$_{20}$-dialkylamino-C$_2$-C$_{10}$-alkyl, C$_1$-C$_{10}$-alkyl-C$_2$-C$_{10}$-alkyl, C$_2$-C$_{20}$-hydroxyalkyl, C$_3$-C$_{12}$-cycloalkyl, C$_4$-C$_{20}$-cycloalkylalkyl, C$_2$-C$_{20}$-alkenyl, C$_4$-C$_{30}$-dialkylaminoalkenyl, C$_3$-C$_{30}$-alkoxyalkenyl, C$_3$-C$_{20}$-hydroxyalkenyl, C$_5$-C$_{20}$-cycloalkylalkenyl, or aryl or C$_7$-C$_{20}$-aralkyl which is unsubstituted or substituted once to five times by C$_1$-C$_8$-alkyl, C$_2$-C$_8$-dialkylamino, C$_1$-C$_8$-alkoxy, hydroxyl, C$_3$-C$_8$-cycloalkyl, C$_4$-C$_{12}$-cycloalkylalkyl, or together an alkylene chain which may be interrupted by nitrogen or oxygen, such as ethylene oxide, propylene oxide, butylene oxide and —CH$_2$—CH(CH$_3$)—O— or polyisobutylene with 1–100 isobutylene units, preferably those of the formula II NH$_2$—(CH$_2$)$_n$—NH$_2$   (II), where n is 2–20.

Diamines of the formula II are preferably primary diamines such as 1,2-ethylenediamine, 1,3-propylenediamine, 1,4-butylenediamine and 1,6-hexamethylenediamine, preferably primary tetraamines such as N,N,N',N'-tetra-aminopropyl-1,2-ethylenediamine, N,N,N',N'-tetraaminopropyl-1,3-propylenediamine, N,N,N'N'-tetraaminopropyl-1,4-butylenediamine and N,N,N',N'-tetraaminopropyl-1,6-hexamethylenediamine, preferably primary octylamines and ammonia.

The radicals R$^7$, R$^8$, R$^9$, R$^{10}$ are C$_1$-C$_6$-alkyl, preferably C$_1$-C$_3$-alkyl such as methyl, ethyl, n-propyl and isopropyl, particularly preferably methyl and ethyl, especially methyl or, preferably, hydrogen, where R$^7$ and R$_8$, and R$^9$ and R$^{10}$, are preferably identical.

R$_{11}$ is specifically C$_1$-C$_{20}$-alkyl, preferably C$_1$-C$_{12}$-alkyl such as 1-phenylpropyl, 2-phenylpropyl, 3-phenylpropyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl and isododecyl, particularly preferably C$_1$-C$_4$-alkyl such as methyl, ethyl, n-propyl isopropyl, n-butyl, isobutyl, sec-butyl and tert-butyl, aryl such as phenyl, 1-naphthyl and 2-naphthyl, preferably phenyl, C$_7$-C$_{20}$-aralkyl, preferably C$_1$-C$_{12}$-phenylalkyl such as benzyl, 1-phenethyl, 2-phenethyl, methyl, ethyl, n-propyl, isopropyl, n-butyl, isobutyl, sec-butyl, 1-phenylbutyl, 2-phenylbutyl, 3-phenylbutyl and 4-phenylbutyl, particularly preferably benzyl, 1-phenethyl and 2-phenethyl, C$_7$-C$_{20}$-alkylaryl, preferably C$_7$-C$_{12}$-alkylphenyl such as 2-methylphenyl, 3-methylphenyl, 4-methylphenyl, 2,4-dimethylphenyl, 2,5-dimethyl, 2,6-dimethylphenyl, 3,4-dimethylphenyl, 3,5-dimethylphenyl, 2,3,4-trimethylphenyl, 2,3,5,-trimethylphenyl, 2,3,6,-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl or polyisobutylene with 1–100, preferably 1–70, particularly preferably 1–50, isobutylene units.

The amines according to the invention are suitable as branching units for nylon 6 [Chem. Mater. 4 (5) (1992) 1000–1004], as diagnostic aids and contrast agents in computerized tomography [Chem. Mark. Rep., Dec. 28, 1992, 242 (26), 19], as standard in gel permeation chromatography, or in cosmetics and the drugs industry as controlled release compounds.

EXAMPLES

The products in the following examples were checked for purity and completeness of the reaction by $^{13}$C- and $^1$H-NMR and mass spectroscopy.

Example 1

443 g (8.35 mol) of acrylonitrile were added dropwise to a vigorously stirred solution of 100 g (1.67 mol) of ethylenediamine in 1176 ml of water at a maximum of 40° C. over the course of 90 min, the mixture was stirred at room temperature for 1 h and at 80° C. for 2 h and then concentrated under reduced pressure at a maximum of 80° C., and the solid residue was filtered off to afford 478 g (1.58 mol) of N,N,N',N'-tetracyanoethyl-1,2-ethylenediamine.

400 ml/h of a mixture of 20% by weight of N,N,N',N'-tetracyanoethyl-1,2-ethylenediamine and 80% by weight of N-methylpyrrolidone and 3500 ml/h ammonia were passed at 1300° C. under 200 bar of hydrogen over 4 liters of a fixed bed catalyst of composition 90% by weight CoO, 5% by weight MnO and 5% by weight P$_2$O$_5$ in a 5 liter fixed bed reactor. Removal of the solvent under reduced pressure and fractional distillation at boiling point 218° C. (6 mbar) resulted in N,N,N',N'-tetraaminopropyl-1,2-ethylenediamine in a yield of 95%.

20 g of N,N,N',N'-tetracyanoethyl-1,2-ethylenediamine and 50 g of Raney nickel (aqueous suspension) were added to a solution of 400 ml of alcohol and water in the ratio 1:1 by volume and 1 ml of 1N NaOH solution under a nitrogen atmosphere in a stirred autoclave. This mixture was hydrogenated under 8 bar of hydrogen at room temperature (25° C.) for about 10 hours.

After the hydrogenation was complete, the catalyst was filtered off and washed with an ethanol/water mixture, and the filtrate was distilled. The conversion was 98% with a selectivity of 22%.

Example 2

300 ml/h of a mixture of 10% by weight N,N,N',N',N'',N''',N'''-octacyanoethyl-N'''',N'''',N'''',N''''-tetraaminopropyl-1,2-ethylenediamine and 90% by weight methanol and 3000 ml/h ammonia were passed at 130° C.

under 200 bar of hydrogen over 4 liters of a fixed bed catalyst of composition 90% by weight CoO, 5% by weight MnO, 5% by weight $P_2O_5$ in a 5 liter fixed bed reactor. Removal of the excess ammonia and methanol resulted quantitatively in N,N,N',N',N",N",N''',N'''-octaaminopropyl-N'''',N'''',N''''',N'''''-tetraaminopropyl-1,2-ethylenediamine (N14-amine).

Example 3

A mixture of 10% by weight N,N,N',N',N",N",N''',N'''-octacyanoethyl-N'''',N'''',N''''',N'''''-tetraaminopropyl-1,2-ethylenediamine and 90% by weight N-methylpyrrolidone and 3000 ml/h ammonia were reacted as in Example 2. Removal of the N-methylpyrrolidone resulted quantitatively in N,N,N',N',N",N",N''',N'''-octaaminopropyl-N'''',N'''',N''''',N'''''-tetraaminopropyl-1,2-ethylenediamine (N14-amine).

Example 4

A fixed bed catalyst of composition 89.6% by weight CoO, 5% by weight MnO, 5% by weight $P_2O_5$ and 0.4% by weight $Na_2O$ was used as in Example 2. N,N,N',N',N",N",N''',N'''-octaaminopropyl-N'''',N'''',N''''',N'''''-tetraaminopropyl-1,2-ethylenediamine was obtained quantitatively (N14-amine).

Example 5

A fixed bed catalyst of composition 89.6% by weight CoO, 5% by weight MnO, 5% by weight $P_2O_5$ and 0.4% by weight $Na_2O$ was used as in Example 3. N,N,N',N',N",N",N''',N'''-octaaminopropyl-N'''',N'''',N''''',N'''''-tetraaminopropyl-1,2-ethylenediamine was obtained quantitatively (N14-amine).

Example 6

As in Example 2, 50 ml/h of a mixture of 10% by weight N,N,N',N',N",N",N''',N'''-octacyanoethyl-N'''',N'''',N''''',N'''''-tetraaminopropyl-1,2-ethylenediamine and 90% by weight N-methylpyrrolidone and 500 ml/h ammonia were reacted on 500 ml of a fixed bed catalyst of composition 89.6% by weight CoO, 5% by weight MnO, 5% by weight $P_2O_5$ and 0.4% by weight $Na_2O$ in a 1 liter fixed bed reactor. Removal of the N-methylpyrrolidone resulted quantitatively in N,N,N',N',N",N,N",N'''-octaaminopropyl-N'''',N'''',N''''', N'''''-tetraaminopropyl-1,2- ethylenediamine (N14-amine).

Example 7

As in Example 2, a mixture of 13% by weight hexadecacyanoethylated N14-amine and 87% by weight N-methylpyrrolidone and 3000 ml/h ammonia were reacted on a fixed bed catalyst of composition 89.6% by weight COo, 5% by weight MnO, 5% by weight $P_2O_5$ and 0.4% by weight $Na_2O$. Removal of the N-methylpyrrolidone resulted quantitatively in hexadecaaminopropylated N14-amine (N30-amine).

Example 8

A mixture of 13% by weight hexadecacyanoethylated N14-amine and 87% by weight of N-methylpyrrolidone and 3000 ml/h ammonia were reacted as in Example 2. Removal of the N-methylpyrrolidone resulted quantitatively in hexadecaaminopropylated N14-amine (N30-amine).

Example 9

50 ml/h of a mixture of 20% by weight hexadecacyanoethylated N14-amine and 80% by weight N-methylpyrrolidone and 500 ml/h ammonia were passed at 130° C. under 200 bar of hydrogen over 500 ml of a fixed bed catalyst of composition 89.6% by weight CoO, 5% by weight MnO, 5% by weight $P_2O_5$ and 0.4% by weight $Na_2O$ in a 1 liter fixed bed reactor. Removal of the N-methylpyrrolidone resulted quantitatively in hexadecaaminopropylated N14-amine (N30-amine).

Example 10

A mixture of 10% by weight hexadecacyanoethylated N14-amine and 90% by weight N-methylpyrrolidone and 500 ml/h ammonia were reacted as in Example 9. Removal of the N-methylpyrrolidone resulted quantitatively in hexadecaaminopropylated N14-amine (N30-.amine).

Example 11

A mixture of 13% by weight of hexadecacyanoethylated N14-amine and 87% by weight N-methylpyrrolidone and 1000 ml/h ammonia were reacted as in Example 9. Hexadecaaminopropylated N14-amine (N30-amine) was obtained quantitatively.

Example 12

As in Example 9, a mixture of 13% by weight hexadecacyanoethylated N14-amine and 87% by weight N-methylpyrrolidone and 1000 ml/h ammonia were reacted using a fixed bed catalyst of composition 90% by weight CoO, 5% by weight MnO and 5% by weight $P_2O_5$. Hexadecaaminopropylated N4-amine (N30-amine) was obtained quantitatively.

We claim:

1. A process for preparing amines by hydrogenation of compounds having at least 3 cyano groups, prepared by addition of acrylonitrile onto ammonia or primary amines, at from 80° to 200° C. under from 5 to 500 bar, which comprises carrying out the hydrogenation continuously on a catalyst which contains from 80 to 98% by weight of cobalt oxide, from 1 to 10% by weight of manganese oxide, from 1 to 10% by weight of phosphorus pentoxide and from 0 to 5% by weight of alkali metal oxide.

2. A process for preparing amines as claimed in claim 1, wherein the hydrogenation is carried out on a catalyst which contains from 86 to 94% by weight of cobalt oxide, from 3 to 7% by weight of manganese oxide and from 3 to 7% by weight of phosphorus pentoxide and from 0 to 5% by weight of alkali metal oxide.

3. A process for preparing amines as claimed in claim 1, wherein the hydrogenation is carried out on a catalyst which contains from 88 to 92% by weight of cobalt oxide, from 4 to 6% by weight of manganese oxide and from 4 to 6% by weight of phosphorus pentoxide and from 0 to 4% by weight of alkali metal oxide.

4. A process for preparing amines as claimed in claim 1, wherein the primary amines used are those of the general formula I $(R^1R^1)N-X-N(R^1R^1)$ (I), where $R^1$ is hydrogen or $(R^2R^2)N-(CH_2)_3-$ and $R^2$ is hydrogen or $(R^3R^3)N-(CH_2)_3-$ and $R^3$ is hydrogen or $(R^4R^4)N-(CH_2)_3-$ and $R^4$ is hydrogen or $(R^5R^5)N-(CH_2)_3-$ and $R^5$ is hydrogen or $(R^6R^6)N-(CH_2)_3-$ and $R^6$ is hydrogen.

x is

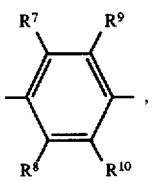,

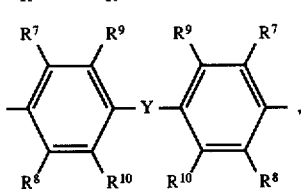,

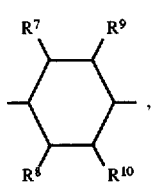,

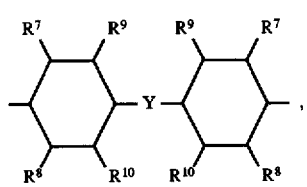,

—(CH$_2$)$_n$—, —(CH$_2$)$_3$—NR$^{11}$—(CH$_2$)$_3$—, C$_2$–C$_{20}$-alkylene, and Y is CR$^7$R$^9$, oxygen, C=O, SO$_2$, n is 2–20, l and k are 2–6 and m is 1–40.

R$^7$, R$^8$, R$^9$, R$^{10}$ are hydrogen or C$_1$–C$_6$-alkyl.

R$^{11}$ is C$_1$–C$_{20}$-alkyl, C$_2$–C$_{20}$-dialkylamino-C$_2$–C$_{10}$-alkyl, C$_1$–C$_{10}$-alkoxy-C$_2$–C$_{10}$-alkyl, C$_2$–C$_{20}$-hydroxyalkyl, C$_3$–C$_{12}$-cycloalkyl, C$_4$–C$_{20}$-cycloalkylalkyl, C$_2$–C$_{20}$-alkenyl, C$_4$–C$_{30}$-dialkylaminoalkenyl, C$_3$–C$_{30}$-alkoxyalkenyl, C$_3$–C$_{20}$-hydroxy-alkenyl, C$_5$–C$_{20}$-cycloalkylalkenyl, or aryl or C$_7$–C$_{20}$-aralkyl which is unsubstituted or substituted once to five times by C$_1$–C$_8$-alkyl, C$_2$–C$_8$-dialkylamino, C$_1$–C$_8$-alkoxy, hydroxyl, C$_3$–C$_8$-cycloalkyl, C$_4$–C$_{12}$-cycloalkylalkyl, or together an alkylene chain which may be interrupted by nitrogen or oxygen, such as ethylene oxide, propylene oxide, butylene oxide and —CH$_2$—CH(CH$_3$)—O— or polyisobutylene with 1–100 isobutylene units.

5. A process for preparing amines as claimed in claim 1, wherein the primary amines used are those of the formula II $$NH_2-(CH_2)_n-NH_2 \quad (II),$$

where n is 2–20.

6. A process for preparing amines as claimed in claim 1, wherein N,N,N',N'-tetraaminopropyl-1,2-ethylenediamine, N,N,N',N'-tetraaminopropyl-1,3-propylene-diamine, N,N,N',N'-tetraaminopropyl-1,4-butylenediamine or N,N,N',N'-tetraaminopropyl-1,6-hexamethylenediamine is used as primary amine.

7. A process for preparing amines as claimed in claim 1, wherein the hydrogenation is carried out at from 100° to 160° C. under from 50 to 300 bar.

8. A cobalt catalyst containing from 80 to 98% by weight of cobalt oxide, from 1 to 10% by weight of manganese oxide, from 1 to 10% by weight of phosphorus pentoxide and from 0 to 5% by weight of alkali metal oxide.

9. A cobalt catalyst containing from 86 to 94% by weight of cobalt oxide, from 3 to 7% by weight of manganese oxide, from 3 to 7% by weight of phosphorus pentoxide and from 0 to 5% by weight of alkali metal oxide.

10. A cobalt catalyst containing from 88 to 92% by weight of cobalt oxide, from 4 to 6% by weight of manganese oxide, from 4 to 6% by weight of phosphorus pentoxide and from 0 to 4% by weight of alkali metal oxide.

* * * * *

UNITED STATES PATENT AND TRADEMARK OFFICE
CERTIFICATE OF CORRECTION

PATENT NO. : 5,750,788
DATED      : May 12, 1998
INVENTOR(S): Häussling et al.

It is certified that error appears in the above-indentified patent and that said Letters Patent is hereby corrected as shown below:

IN THE CLAIMS:

In Claim 4, Column 7, line 33: after "alkylene," and before line 34 which begins "and Y", insert the formula -- $-(CH_2)_l-[O-(CH_2)_k]_m-O-(CH_2)_l)-$ --.

Signed and Sealed this

Twenty-first Day of July, 1998

Attest:

BRUCE LEHMAN

*Attesting Officer*   *Commissioner of Patents and Trademarks*